US010863972B2

(12) United States Patent
Guenther

(10) Patent No.: US 10,863,972 B2
(45) Date of Patent: Dec. 15, 2020

(54) IMAGE DOMAIN ULTRASOUND IMAGING DENOISING FILTER

(71) Applicant: B-K Medical Aps, Herlev (DK)

(72) Inventor: Drake A. Guenther, Charlottesville, VA (US)

(73) Assignee: B-K Medical ApS, Herlev (DK)

( * ) Notice: Subject to any disclaimer, the term of this patent is extended or adjusted under 35 U.S.C. 154(b) by 930 days.

(21) Appl. No.: 15/469,733

(22) Filed: Mar. 27, 2017

(65) Prior Publication Data

US 2018/0271498 A1  Sep. 27, 2018

(51) Int. Cl.
*A61B 8/08* (2006.01)
*G01S 7/52* (2006.01)
*G01S 15/89* (2006.01)
*A61B 8/00* (2006.01)

(52) U.S. Cl.
CPC .......... *A61B 8/5269* (2013.01); *A61B 8/5207* (2013.01); *G01S 7/52046* (2013.01); *G01S 7/52077* (2013.01); *G01S 15/8915* (2013.01); *G01S 15/8995* (2013.01); *A61B 8/4488* (2013.01)

(58) Field of Classification Search
CPC ... A61B 8/5269; A61B 8/5207; A61B 8/4488; G01S 15/8995; G01S 15/8915; G01S 7/52077; G01S 7/52046
See application file for complete search history.

(56) References Cited

U.S. PATENT DOCUMENTS

| 2015/0320395 A1* | 11/2015 | Sato | A61B 8/06 600/455 |
| 2015/0366540 A1* | 12/2015 | Sato | A61B 8/5207 600/453 |
| 2017/0086793 A1* | 3/2017 | Sato | A61B 8/4416 |

OTHER PUBLICATIONS

Demene, et al. Spatiotemporal Clutter Filtering of Ultrafast Ultrasound Data Highly Increases Doppler and fUltrasound Sensitivity, DOI 10.1109/TMI.2015.24238634, IEEE Transactions on Medical Imaging 2015.
Mauldin, et al. A Singluar Value Filter for Rejection of Stationary Artifact in Medical Ultrasound, 2010 IEEE International Ultrasonics Symposium Proc., 2010.

(Continued)

*Primary Examiner* — Peter Luong
(74) *Attorney, Agent, or Firm* — Anthony M. Del Zoppo, III; Daugherty & Del Zoppo Co., LPA

(57) ABSTRACT

An apparatus includes a memory device with computer readable instructions and a processor configured to execute the computer readable instructions encoded on the memory device. The processor, in response to executing the computer readable instructions, obtains an ensemble of ultrasound images with diversity in an ensemble dimension, extracts a sub-set of data from each of the images, constructs a data matrix with the extracted data, wherein the data matrix has a dimension of space versus the ensemble dimension, identifies a largest eigenvalue(s) and a corresponding eigenvector(s) in the data matrix, computes a coherent signal projection matrix with the identified corresponding eigen vector(s), filters the data matrix with the coherent signal projection, and generates an ultrasound image with the filtered data matrix.

20 Claims, 6 Drawing Sheets

(56) References Cited

OTHER PUBLICATIONS

Montaldo, et al., Coherent Plane-Wave Compouding for Very High Frame Rate Ultrasonography and Transient Elastography, IEEE Transactions on US, Ferroelectrics and Frequency Control, vol. 56, No. 3, Mar. 2009.
Shuwei, et al., Structure-oriented singular value decomposition for random noise attenuation of seismic data, DOI: 10.1088/1742-2132/12/2/262, Journal of Geophysics and Engineering Apr. 2015.

* cited by examiner

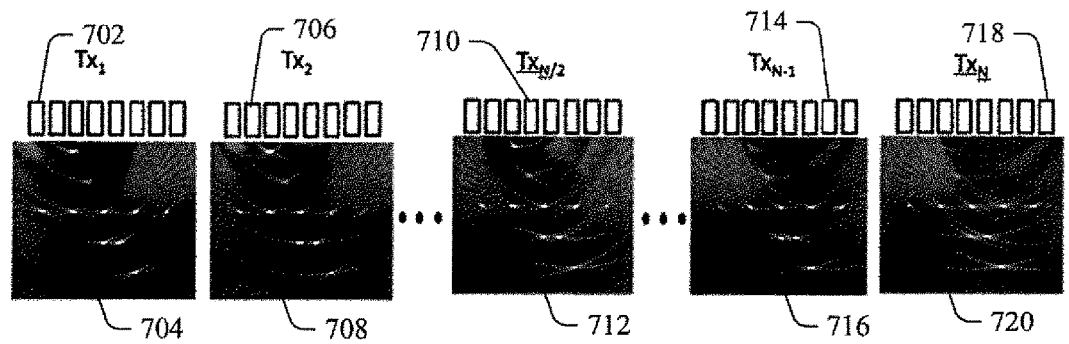
FIGURE 7
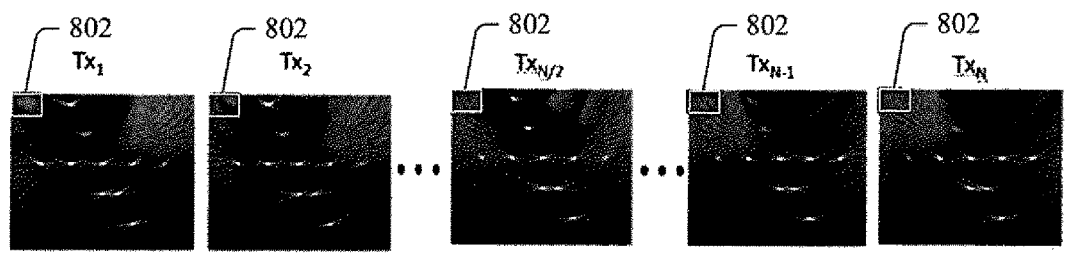
FIGURE 8
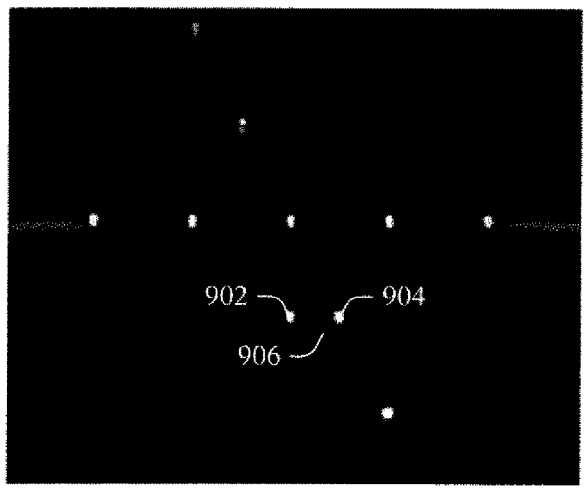 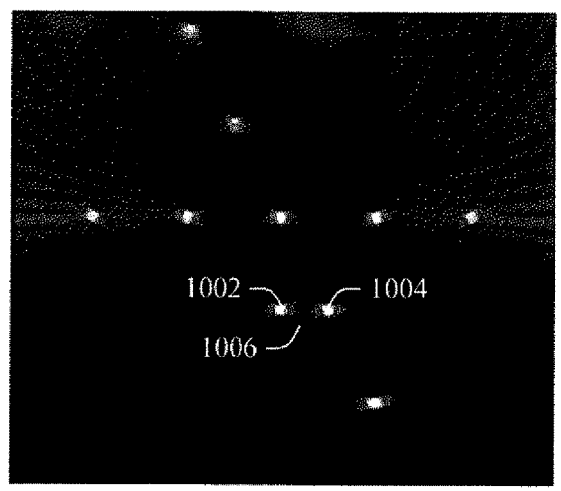
FIGURE 9          FIGURE 10

IMAGE DOMAIN ULTRASOUND IMAGING DENOISING FILTER

TECHNICAL FIELD

The following generally relates to ultrasound imaging and more particularly to an image domain ultrasound imaging denoising filter.

BACKGROUND

Ultrasound imaging provides information about interior characteristics of an object or subject. An ultrasound imaging system has included at least a transducer array with one or more transducing elements excitable to transmit an ultrasound signal (e.g., a pressure wave) into the object or subject. As the signal traverses (static and/or moving) structure therein, portions of the signal are attenuated, scattered, and/or reflected off the structure, with some of the reflections (echoes or echo signals) traversing back to the one or more elements. The one or more elements receive the echoes and convert them into electrical signals indicative thereof. The electrical signals are processed to generate one or more images of the interior characteristics of the object or subject.

The quality of an ultrasound image depends on several factors. Noise sources such as electronic or random noise, as well as off-axis and reverberation scattering from near field anatomical structures, may degrade image quality. These types of noise sources tend to clutter the image, obscuring detail and limiting contrast resolution. The literature discusses various aperture domain (pre-beamformed) approaches aimed at reducing these noise sources. Spatial compounding improves contrast resolution by incoherently compounding images acquired at different interrogation/reception angles. Short lag spatial coherence and phase coherence compute local data statistics on the focused data.

Unfortunately, these and other aperture domain approaches are not well-suited for real-time imaging. That is, although these approaches may increase the signal-to-noise ratio (SNR), reduce clutter, and improve contrast resolution, since they process pre-beamformed electrical signals (i.e. they are employed in the aperture domain), they require high computational complexity at least because they process every data point, which can be a challenge to implement in real time on an ultrasound imaging system architecture. As such, there is an unresolved need for another approach(s).

SUMMARY

Aspects of the application address the above matters, and others.

In one aspect, an apparatus includes a memory device with computer readable instructions and a processor configured to execute the computer readable instructions encoded on the memory device. The processor, in response to executing the computer readable instructions, obtains an ensemble of ultrasound images with diversity in an ensemble dimension, extracts a sub-set of data from each of the images, constructs a data matrix with the extracted data, wherein the data matrix has a dimension of space versus the ensemble dimension, identifies a largest eigenvalue(s) and a corresponding eigenvector(s) in the data matrix, computes a coherent signal projection matrix with the identified corresponding eigenvector(s), filters the data matrix with the coherent signal projection, and generates an ultrasound image with the filtered data matrix.

In another aspect, a method includes extracting a sub-set of data from each image of an ensemble of ultrasound images having diversity in an ensemble dimension, constructing a data matrix with the extracted data, wherein the data matrix has a dimension of space versus the ensemble dimension, identifying largest eigenvalue(s) in the data matrix, computing a coherent signal projection matrix with eigenvector(s) of the identified eigenvalue(s), filtering the data matrix with the coherent signal projection, and generating a decluttered ultrasound image with the filtered data.

In another aspect, a computer readable medium is encoded with computer executable instructions which when executed by a processor causes the processor to: extract a sub-set of data from each image of an ensemble of ultrasound images having diversity in an ensemble dimension, construct a data matrix with the extracted data, wherein the data matrix has a dimension of space versus the ensemble dimension, compute a covariance matrix with the data matrix, identify largest eigenvalue(s) and a corresponding eigenvector(s) in the covariance matrix, compute a coherent signal projection matrix with the eigenvector(s) of the identified eigenvalue(s), filter the data matrix with the coherent signal projection, compound the filtered data across the ensemble dimension, and generate a decluttered ultrasound image with the compounded filtered data.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which:

FIG. 7 shows another example of an ensemble of ultrasound images across transmit element in accordance with an embodiment described herein;

FIG. 8 shows another example of extracting data from a sub-region of the ensemble of ultrasound images in accordance with an embodiment described herein;

FIG. 9 illustrates an example image after applying the filter described herein in accordance with an embodiment described herein;

FIG. 10 illustrates a comparison image without applying the filter described herein in accordance with an embodiment described herein;

DETAILED DESCRIPTION

Figure 1:
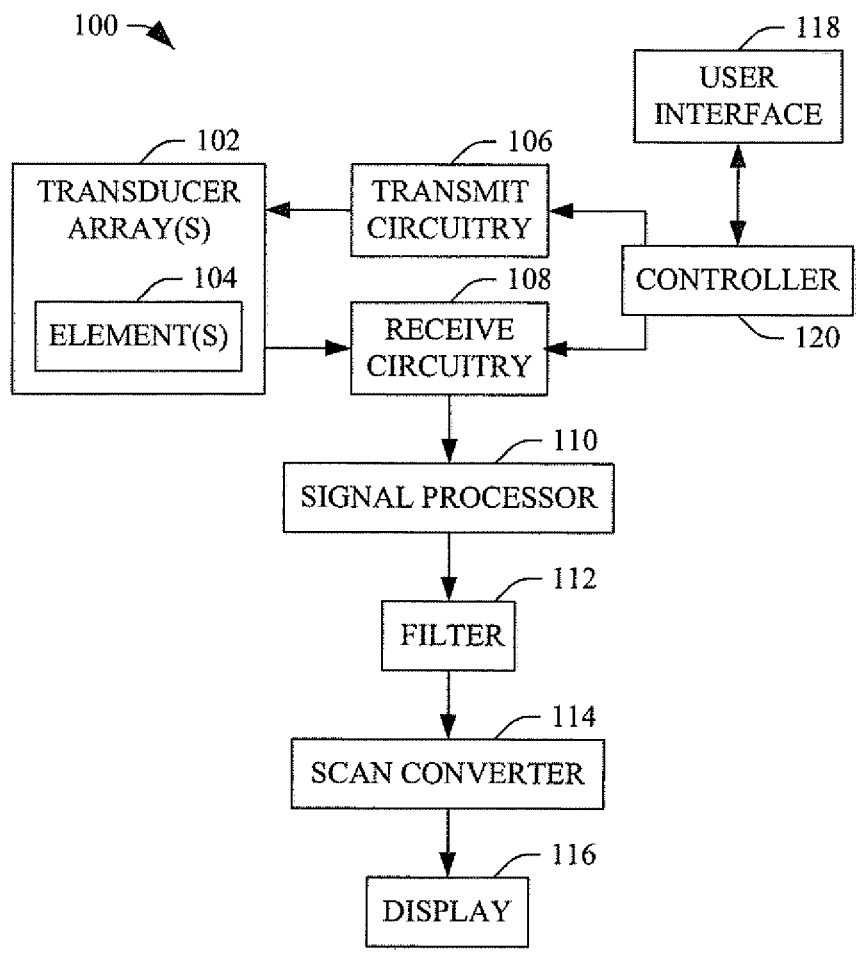
FIG. 1 schematically illustrates an example ultrasound imaging system in accordance with an embodiment described herein.

FIG. 1 schematically illustrates an imaging 100 system such as an ultrasound imaging system.

The illustrated imaging system 100 includes one or more transducer arrays 102 of one or more transducer elements 104. The one or more transducer arrays 102 can include a 1-D array, a 1.5-D array, a 1.75-D array, a 2-D array, and/or other array(s). Examples of arrays include 64, 128, 256, 32×32, 64×64, and/or other dimension arrays, including circular, elliptical, rectangular, irregular, etc. The transducer array can be linear, curved, and/or otherwise shaped, fully populated, sparse, etc.

The elements 104 are configured to transmit ultrasound signals in response to being excited by an electrical signal or pulse. Examples of transmissions include plane wave, diverging wave, single element, etc. The elements 104 are further configured to receive echoes (echo signals) and generate electrical signals indicative of the received echo signals. An echo, generally, is a result of the interaction between a transmitted ultrasound signal and static and/or moving structure, such as organ cells, soft tissue, flowing blood cells in a vessel, etc.

The ultrasound imaging system 100 further includes transmit circuitry 106 that controls excitation of the one or more transducer elements 104 of the transducer arrays 102 via the excitation electrical signal or pulse to transmit ultrasound signals. The ultrasound imaging system 100 further includes receive circuitry 108 that receives the electrical signals generated by the elements 104 and routes the signals to other components of the ultrasound imaging system 100 for processing.

The ultrasound imaging system 100 further includes a signal processor 110 configured to process the electrical signals and produce an ensemble of images (e.g., using delay and sum focusing) that express signal diversity in an ensemble dimension (e.g., interrogated spatial frequency in the case of plane wave compounding) where the signal of interest is coherent across the ensemble, and clutter, reverberation, and/or electronic noise are incoherent across the ensemble. Generally, this includes images produced using plane wave compounding datasets where an ensemble is acquired with different plane wave transmissions with varying tilt angles, synthetic aperture datasets, transmit/receive spatial compounding datasets, datasets with different apodizations applied such as those used in dual apodization with cross correlation, and/or other approaches.

The ultrasound imaging system 100 further includes filter 112 configured to filter in the post-processed/image domain (the signals after being processed by the signal processor 110), in contrast to the pre-processed signals, or pre-processed/raw data domain (the signals before being processed by the signal processor 110). As described in greater detail below, in one instance the filter 112 employs an algorithm that removes incoherent-across-the-ensemble noise sources.

A suitable algorithm is based on the following model: $x=s+c+n$, where the parameter s represents a signal component, parameter c represents a clutter component and the parameter n represents a noise component. With the model x, a data matrix X can be constructed by making N observations of the signal in such a way that the desired signal component s is stationary across the observations and coherent whereas the clutter component c and the noise component n are non-stationary and incoherent across the observations.

Such is the case, e.g., when compounding images resulting from different plane waves or different transmit/receive elements in synthetic aperture. In such cases, when performing an eigenvalue decomposition on the observation matrix X, the signal of interest s will be associated with a largest eigenvalue(s). As described in greater detail below, subspace projection filtering of the matrix X onto the estimated signal subspace can then be performed. As utilized herein, this filtering is referred to herein as Singular Value Decomposition Polarization (SVDP) filtering at least because the filter preferentially passes signals that are coherent ("straight lines") across the N observations. Generally, the approach described herein applies to any approach that compounds in the image domain, such as plane wave, diverging wave, virtual source, single element, synthetic aperture sequential beamforming (SASB), retrospective transmit focusing, etc. imaging.

In one instance, the filter 112 can reduce electronic noise, clutter, and/or reverberation in ultrasound images. Additionally or alternatively, the filter 112 can reduce computational overhead, relative to filtering in the aperture, pre-processed data domain, at least because the data space (the amount of data) is reduced in dimensionality as compared to filtering in the aperture, pre-processed domain. In one instance, the data can additionally or alternatively be projected onto an orthogonal "null or clutter" subspace, which could also be useful and could highlight regions of strong off-axis reflections or anisotropic scattering.

The ultrasound imaging system 100 further includes a scan converter 114 and a display 116. The scan converter 114 is configured to convert the filtered images for display via the display 116, e.g., by converting the data to the coordinate system of the display 116. The ultrasound imaging system 100 further includes a user interface 118, which includes an input device(s) (e.g., a mouse, a keyboard, touch controls, etc.), which allows for user interaction with the system 100, e.g., to select an imaging and/or data processing of interest.

The ultrasound imaging system 100 further includes a controller 120. The controller is configured to control at least the transmit circuitry 106, the receive circuitry 108, the signal processor 110, and the filter 112, e.g. In one instance, such control is based on an imaging mode, such as A-mode, B-mode, C-scan, and/or other ultrasound imaging mode, and/or image formation algorithm such as plane wave compounding, synthetic aperture, transmit/receive spatial compounding, multi-apodization, and/or other image formation algorithm.

In one instance, the signal processor 110 and/or the filter 112 is implemented through hardware (e.g., an ASIC, IC, etc.) and/or one or more computer processors (e.g., a microprocessor, a control processing unit (CPU), etc.) executing one or more computer readable instructions encoded or embodied on computer readable storage medium (which excludes transitory medium), such as physical computer memory, which causes the one or more computer processors to carry out the various acts and/or functions described herein and/or other acts and/or functions.

Figure 2:
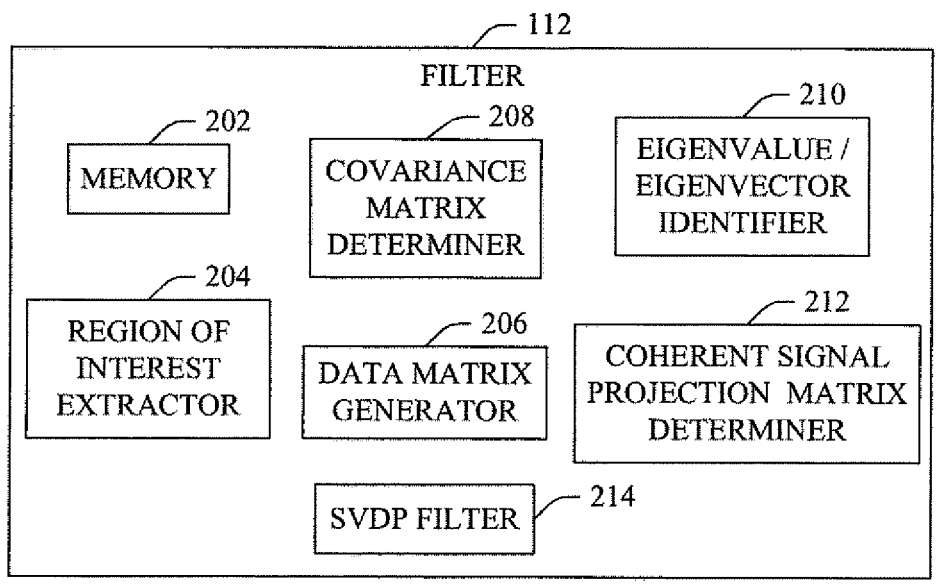
FIG. 2 illustrates an example filter of the ultrasound imaging system in accordance with an embodiment described herein.

FIG. 2 schematically illustrates an example of the filter 112. For sake of explanation, this example is described in connection with plane wave compounding. However, it is to be understood that the approach described herein is applicable to any scenario that satisfies the signal model described herein.

For plane wave compounding, the transducer array 102 (e.g., all of the elements 104) is controlled to successively transmit single plane waves with different linear tilts or phases across the array 102. However, similar to synthetic aperture approaches, a focus can be applied everywhere on transmit retrospectively by applying the appropriate delays. With coherent plane wave compounding, only one transmit event is necessary to from a complete image, and high quality ultrasound images can be acquired with high pulse repetition frequencies (PRFs) (e.g., >10 kHz).

Figure 3:
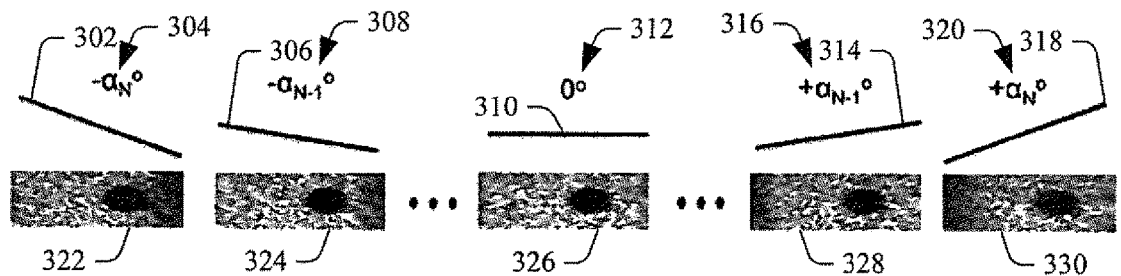
FIG. 3 shows an example of an ensemble of 2-D ultrasound images across plane wave angle in accordance with an embodiment described herein.

An example is shown in FIG. 3 for an ensemble over 2N+1 angles (N represents non-zero angles). A first single plane wave transmission 302 is at a first angle 304)($-\alpha_N°$), a next single plane wave transmission 306 is at a next angle 308 ($-\alpha_{N-1}°$), . . . , a subsequent single plane wave transmission 310 is at a subsequent angle 312 (0°), . . . , a subsequent single plane wave transmission 314 is at a subsequent angle 316 ($+\alpha_{N-1}°$), and a next single plane wave transmission 318 is at a next angle 320 ($+\alpha_N°$). For each of the angles 304, 308, . . . , 312, . . . , 316 and 320, the electrical signals generated for the received echoes are processed, creating 2N+1 images 322, 324, . . . , 326, . . . , 328 and 330.

Returning to FIG. 2 and with continuing reference to FIG. 3, in the illustrated embodiment, the images 322, 324, . . . , 326, . . . , 328 and 330 are stored in memory 202. In the illustrated embodiment, the memory 202 is shown in the filter 112. Alternatively, or additionally, the memory 202 is located external to the filter 112. This includes external to the filter 112 and inside of the imaging system 100 and/or external to the filter 112 and outside of the imaging system 100.

Figure 4:
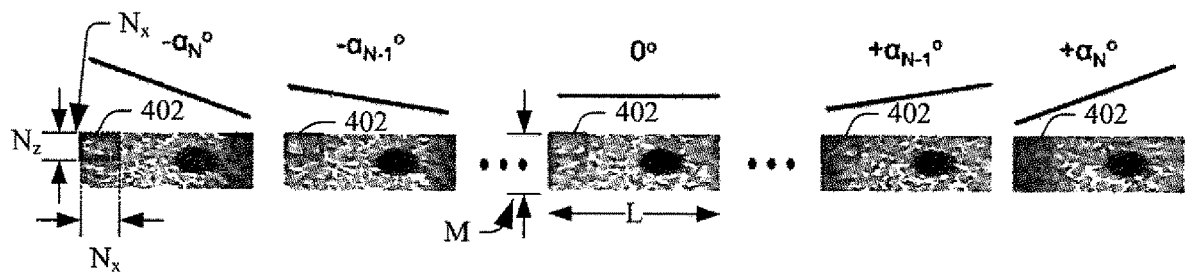
FIG. 4 shows an example of extracting data from a sub-region of the ensemble of 2-D ultrasound images in accordance with an embodiment described herein.

A region of interest (ROI) extractor 204 extracts image values for a predetermined region of each of the images 322, 324, . . . , 326, . . . , 328 and 330. In FIG. 4, each image is M×L, where M is a number of data points in the axial direction and L a number of data points in the azimuth/lateral direction. In the illustrated example, the ROI extractor 204 extracts an $N_x \times N_z$ region 402, where $N_z$ is less then M and $N_x$ is less than L, from each image. In a variation, $N_z$ equals M. In another variation, $N_x$ equals L. In another variation, $N_z$ equals M and $N_x$ equals L. In one instance, $N_z$ equals a wavelength and $N_x$ equals a wavelength or less, depending upon the lateral resolution of the imaging system.

Returning to FIG. 2, a data matrix generator 206 populates a data matrix S with the extracted values. In one instance, the data matrix S is a $N_x N_z$, x $N_\alpha$, where $N_\alpha$, represents the 2N+1 angles and $N_x N_z$ represent a length of the extracted data. For example, in one instance, each column of the data matrix S corresponds to one of the images/2N+1 angles, and each row along a column stores a different one of the extracted $N_x N_z$ values. In a variation, each row of the data matrix S corresponds to one of the images/2N+1 angles, and each column along a row stores a different one of the extracted $N_x N_z$ values.

A covariance matrix determiner 208 computes a covariance matrix $S^H S$ from the data matrix S, where $S^H$ is a complex conjugate of S. An eigenvalue/eigenvector identifier 210 performs an eigenvalue decomposition of the covariance matrix $S^H S$, e.g., using: $R = S^H S = V \Lambda V$, where a matrix $\Lambda$ is a diagonal matrix with a kth entry being a kth eigenvalue $\lambda_k$ and V are eigenvectors. For each eigenvalue, there is an associated eigenvector in a kth column of V. The eigenvalue/eigenvector identifier 210 also identifies a largest eigenvalue(s) and an eigen vector(s) corresponding thereto. In one instance, only a single eigenvalue and eigen vector are identified. In another instance, two or more eigenvalues and eigenvectors are identified.

A coherent signal projection matrix determiner 212 constructs a coherent signal projection matrix. In one instance, the coherent signal projection matrix is computed as: $P_s = \Sigma_1^{k \leq 2N} v_k v_k^H$, where $v_k$ is the kth eigenvector an $v_k^H$ is the complex conjugate of $v_k$. The actual number of eigenvectors used to compute the coherent signal projection matrix $P_s$ can be predetermined or data adaptive, e.g., adaptively determining an eigenvalue/eigenvector cutoff by computing eigenvalue ratios and then setting a threshold. A singular value decomposition polarization (SVDP) filter 214 polarizes, de-clutters, and de-noises the data matrix S, producing $\tilde{S}$. In one instance, SVDP filter 214 computes $\tilde{S}$ as: $\tilde{S} = S P_s w$, where the vector w is a weighting vector across transmit angle, which could also be data adaptive. A vector w of all 1's corresponds to no transmit angle weighting.

In this example, the vector w compounds the data across the 2N+1 angles, producing a $N_x N_z \times 1$ (or $1 \times N_x N_z$) vector $\tilde{S}$. The compounded data in the vector is then used to populate an $N_x \times N_z$ region 402 of a compounded image. This is repeated for a plurality of other $N_x \times N_z$ regions of the 2N+1 images 322, 324, . . . , 326, . . . , 328 and 330, until a complete compounded image of size M×L, which is the same size as the original the 2N+1 images 322, 324, . . . , 326, . . . , 328 and 330.

In general, the SVDP filter 214 will make each image in the ensemble better. Above, the filtered images are compounded to make a "best" image. Additionally or alternatively, the filtered images can be used to make a "better" X-degree plane wave image, where X represent an angle of interest. For instance, the filtered images can be used to make a "better" 0-degree plane wave image (X=0), for example, by extracting just the 0-degree filtered image from the ensemble filtered dataset.

In the above example, each of the regions 402 is $N_x \times N_z$. In a variation, at least one of the regions 402 is greater or smaller than $N_x \times N_z$. In one instance, the regions 402 abut each other. In a variation, at least one the regions 402 overlaps another region. Where there is overlap, in one instance, the filtered data that overlaps is averaged. In another instance, the filtered data that overlaps is weightily averaged. In another instance, only one of the sets of the filtered data that overlaps is utilized for the overlap region.

In another variation, the covariance matrix determiner 208 is omitted, and singular value decomposition (SVD) filtering is applied to the data matrix S.

Figure 5:
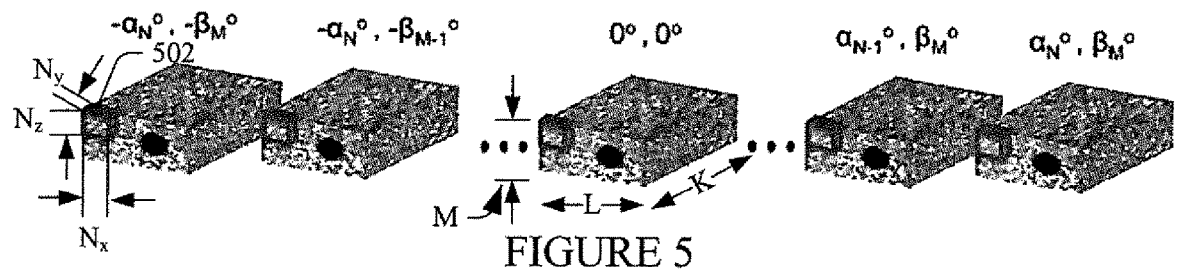
FIG. 5 shows an example of an ensemble of 3-D ultrasound images and extracting data therefrom in accordance with an embodiment described herein.

FIGS. 2-4 describe a 2-D example utilizing an ensemble of 2-D ultrasound images. In a variation, this approach can also be utilized with an ensemble of 1-D ultrasound images (e.g., M-mode lines) and/or an ensemble of 3-D ultrasound images by including the elevation dimension. An example of the 3-D variation is described in connection with in FIG. 5, where the plane waves can be titled in two directions represented by the angle α (as described above) and an angle β. In this case, the ROI extractor 204 extracts values for a predetermined 3-D region 502 of size $N_x \times N_y \times N_z$ region 402, where $N_x$, $N_y$, and $N_z$ respectively are equal to or less than L, M, and K from each image volume of dimension L×M×K.

The data matrix generator 206 populates the matrix S with the extracted values, which, in this example, produces a $N_x N_y N_z \times N_\alpha N_\beta$ or $N_\alpha N_\beta \times N_x N_y N_z$ data matrix S. The covariance matrix determiner 208 computes a covariance matrix $S^H S$ as described herein. The eigenvalue/eigenvector identifier 210 performs an eigenvalue decomposition and identifies a largest eigenvalue(s) and an eigenvector(s) corresponding thereto as described herein. The coherent signal projection matrix determiner 212 constructs a coherent signal projection matrix as described herein. The SVDP filter 214 polarizes, de-clutters, and de-noises the 3-D data matrix S producing a $N_x N_y N_z \times 1$ vector Š as described herein.

In this case, the data is compounded across angles α and β, e.g., by summing across each of the angles. The compounded data is then used to populate an $N_x \times N_y \times N_z$ region 502 of a compounded image volume, as described herein. This is repeated for a plurality of other $N_x \times N_y \times N_z$ (or other size) regions of the image volumes, until a complete compounded image volume of size L×M×K.

Figure 6:
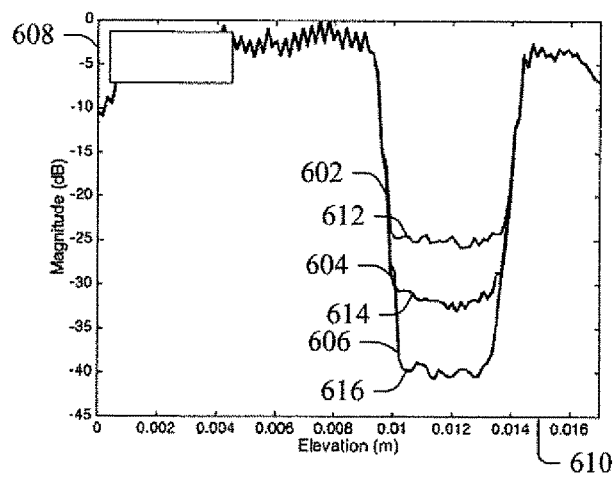
FIG. 6 shows plots of summed energy across an image in accordance with an embodiment described herein.

An example of results is illustrated in FIG. 6. These results were produced for a synthetic volume dataset simulating a C-plane platform and working on a 2-D plane wave compounding dataset. A 2.5 millimeter (mm) diameter vessel was embedded in a homogenous, speckle generating background. Plane wave transmissions ranging from −26° to +26° in 2° increments in both the X and Y dimensions were simulated. This resulted in 53 unique steering angles on transmit. Standard delay and sum focusing with a dynamic hamming window was used on receive.

FIG. 6 shows plots 602, 604 and 606 of summed energy across a C-plane image. A first axis 608 represents magnitude in units of decibels (dB), and a second axis 610 represents elevation in a middle of the vessel. The first plot 602 represents a cross sectional energy of a C-plane image generated using plane wave compounding (53 angles) with noisy data (25 dB SNR per transmit angle image). To show the affect the noise had on the data, the second plot 604 represents a cross sectional energy of the same C-plane image generated using plane wave compounding with no noise. The third plot 606 represents a cross sectional energy of a C-plane image generated using plane wave compounding after applying the SVDP filtering approach described herein.

Regions 616, 614 and 616 respectively show the summed energy across a cross section of the vessel at a constant depth in the C-plane image. As illustrated, the region 616 of the plot 606 for the SVDP filtered data clearly shows decluttering inside the vessel by the polarization filter. Furthermore, the region 614 of the plot 606 for the SVDP filtered data also shows that in this example the SVDP filter improves contrast resolution even more than the dataset with no noise (the region 614) as the SVDP filter is able to not only mitigate electronic noise but also mitigate the effects of sidelobes/clutter in the imaging impulse response. In this example, the SVDP filter improves contrast by roughly 15 dB compared to the noisy image and 7-8 dB compared to the noiseless image.

FIGS. 7-11 schematically illustrates an example where the ensemble is across synthetic aperture profile datasets. For synthetic aperture imaging, the transducer array 102 is controlled to successively transmit via a different single element 104 and receive with all of the elements 104.

In FIG. 7, the ensemble is over T transmits (T represents the total number of transmits). A first element 702 transmits and the data received by all of the elements 104 produces a first image 704, a next element 706 transmits and the data received by all of the elements 104 produces a next image 708, . . . , a subsequent element 710 transmits and the data received by all of the elements 104 produces a subsequent image 712, . . . , a subsequent element 714 transmits and the data received by all of the elements 104 produces a subsequent image 716, and a next element 718 transmits and the data received by all of the elements 104 produces a next image 720.

In FIG. 8, the ROI extractor 204 extracts data from regions 802 respectively from the images 704, 708, . . . , 712, . . . , 716 and 720, as described in connection with FIG. 4. The data matrix generator 206 populates a data matrix S with the extracted values, as described herein. However, the data matrix S in this example represents space versus transmission or element. The eigenvalue/eigenvector identifier 210, the covariance matrix determiner 208, the coherent signal projection matrix determiner 212, the SVDP filter 214, and compounder 216 are operated as described in connection with FIG. 2, but with the data matrix S produced from the synthetic aperture datasets.

Figure 11:
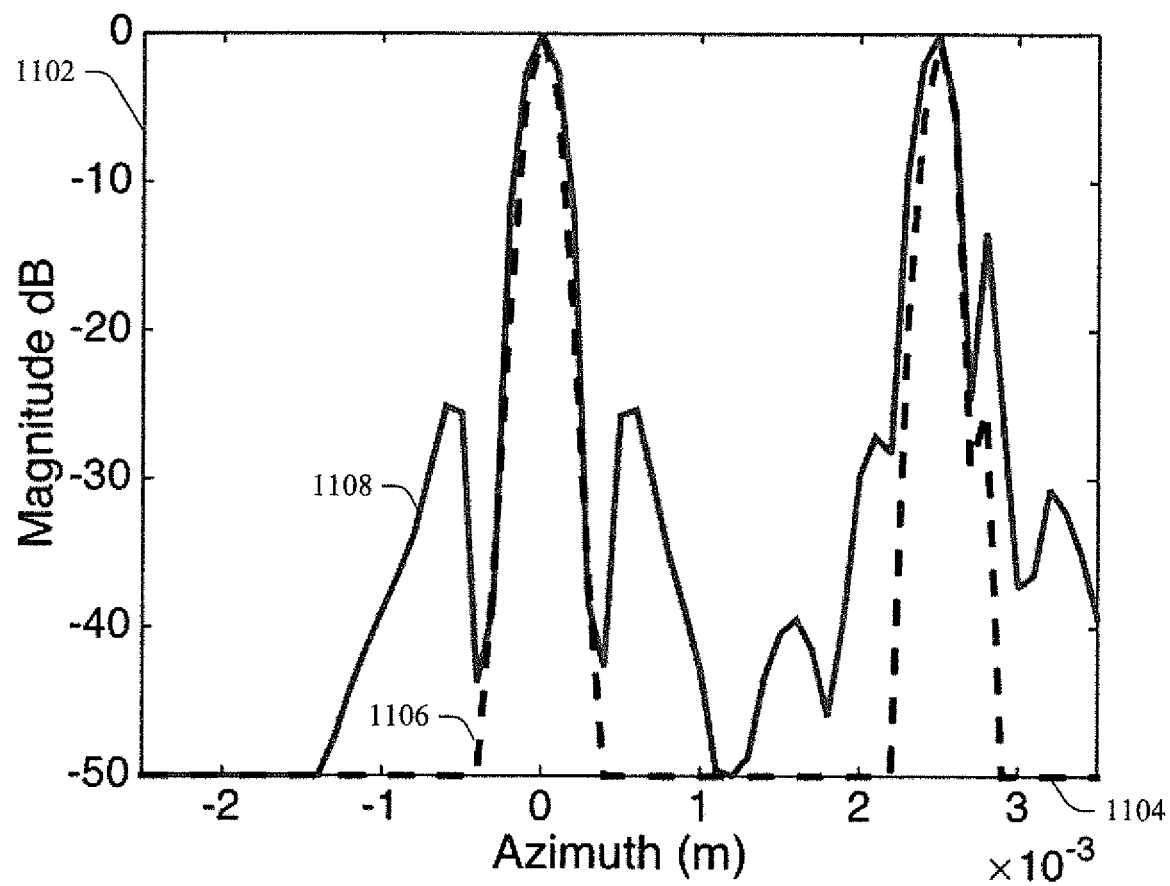
FIG. 11 shows lateral beamplots for point targets in the images of FIGS. 9 and 10 in accordance with an embodiment described herein.

FIG. 9 shows a resulting decluttered image. For comparison, FIG. 10 shows a resulting image formed by summing ensemble 704, 708, . . . , 712, . . . , 716 and 720, where the SVDP filter 214 is not applied. FIG. 11 shows lateral beamplots for point targets 902 and 904 in a region 906 of FIG. 9 and points targets 1002 and 1004 in a region 1006 of FIG. 10. A first axes 1102 represents magnitude in units of dB, and a second axes 1104 represents azimuth. A first beamplot 1106 is for the SVDP filter data, and a second beamplot 1108 is for the data that was not SVDP filtered. FIGS. 9-11 show the SVDP filtering mitigates clutter and sidelobes, relative to a configuration in which the SVDP filter is not applied.

In FIGS. 2-6, the data in the data matrix S represents space versus angle from an ensemble of plane wave images. In FIGS. 7-11, the data matrix S represents space versus synthetic aperture profile. Where the ensemble includes datasets with different apodizations, the data matrix S represents space versus apodization. Where the ensemble includes datasets generated in response to transmissions from diverging waves, the data matrix S represents space versus diverging wave. Where the ensemble includes datasets generated with a fixed transmit focus (e.g., SASB, retrospective, etc. transmit focusing, where A-lines are compounded, the data matrix S represents space versus transmit event. Where the ensemble includes datasets generated from a first stage beamformer (e.g., SASB, Retrospective, etc. transmit focusing, micro-beamforming where a first stage beamformer is implemented to reduce the data throughput, and then outputs from the first stage are coherently compounded to produce a better image in the second stage beamformer), the data matrix S represents space versus first stage beamformer output. The data matrix S does not represent space versus time in any of these variations—angle, synthetic aperture profile, apodization, diverging wave, transmit event, or first stage beamformer output.

Figure 12:
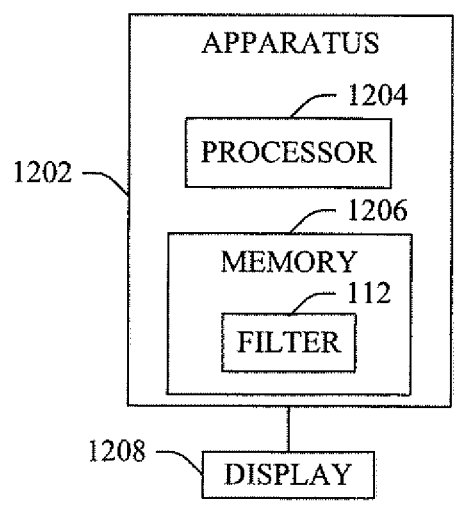
FIG. 12 schematically illustrates an example apparatus configure to implement the filter described herein in accordance with an embodiment described herein.

FIG. 12 schematically illustrates an embodiment in which an apparatus 1202 (e.g., a desktop computer, a laptop computer, a tablet computer, a smartphone, etc.) includes the filter 112. The apparatus 1202 includes at least a processor 1204 and a memory device (memory) 1206, which stored computer readable instructions for implementing the filter 112. The processor 1204 executes the computer readable instructions, which causes the processor 1204 to filter the ensemble, which can be from the signal processor 110 or other memory. The processor 1204 produces the decluttered image, which can be displayed via a display 1208, the display 116, and/or other display, and/or saved to memory.

Figure 13:
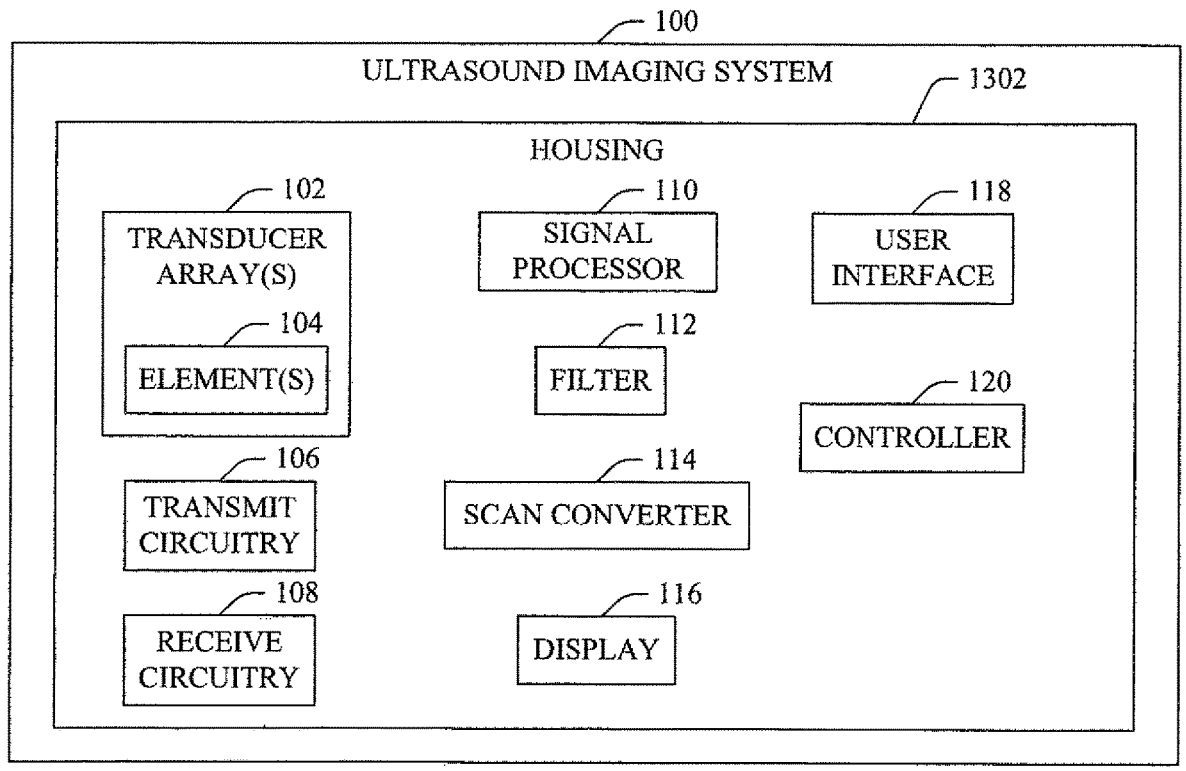
FIG. 13 schematically illustrates another example ultrasound imaging system in accordance with an embodiment described herein.

In FIG. 13, the ultrasound imaging system 100 is a hand-held device with a single enclosure or housing 1302, which houses and physically supports the components described in connection with FIG. 1. An example of a hand-held device is described in U.S. Pat. No. 7,699,776 to Walker et al., entitled "Intuitive Ultrasonic Imaging System and Related Method Thereof," and filed on Mar. 6, 2003, which is incorporated herein in its entirety by reference. Other hand-held devices are also contemplated herein.

Figure 14:
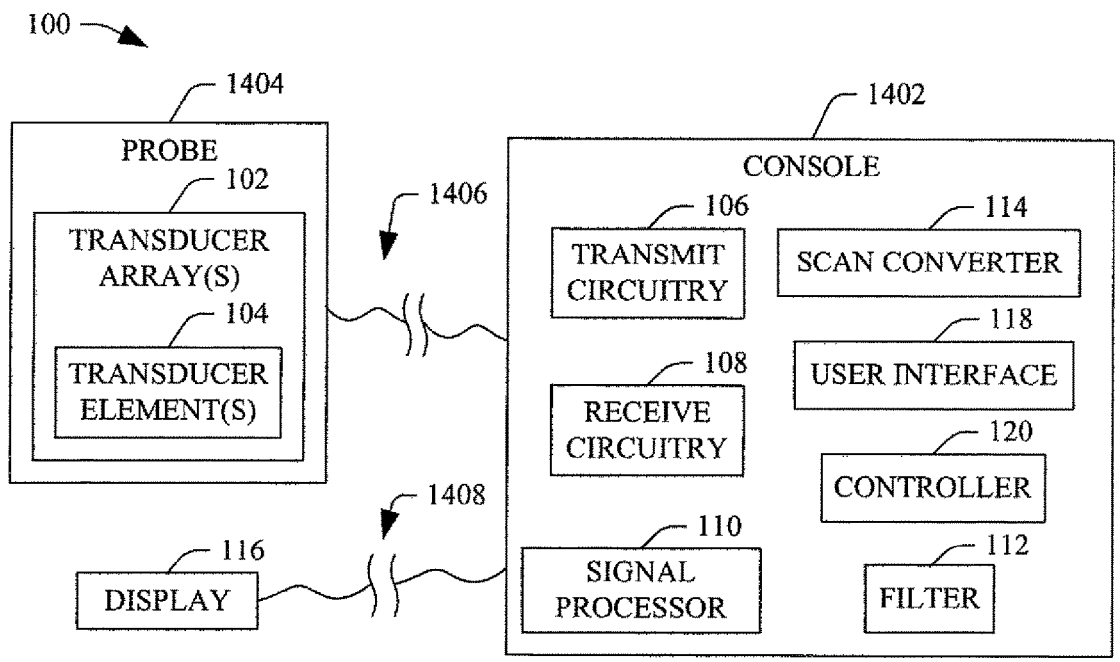
FIG. 14 schematically illustrates another example ultrasound imaging system in accordance with an embodiment described herein.

In FIG. 14, the ultrasound imaging system 100 includes a console 1402 and a separate transducer probe 1404 that interfaces therewith via a communication channel 1406. The ultrasound transducer probe 1404 includes the one or more transducer arrays 102 with the one or more transducer elements 104. The console 1402 includes the transmit circuitry 106, the receive circuitry 108, the signal processor 110, the filter 112, the scan converter 114, the user interface 118, and the controller 120. The display 116 is shown separate from the console 1402 and the transducer probe 1404 and interfaced with the console 1402 via a communication channel 1408.

Figure 15:
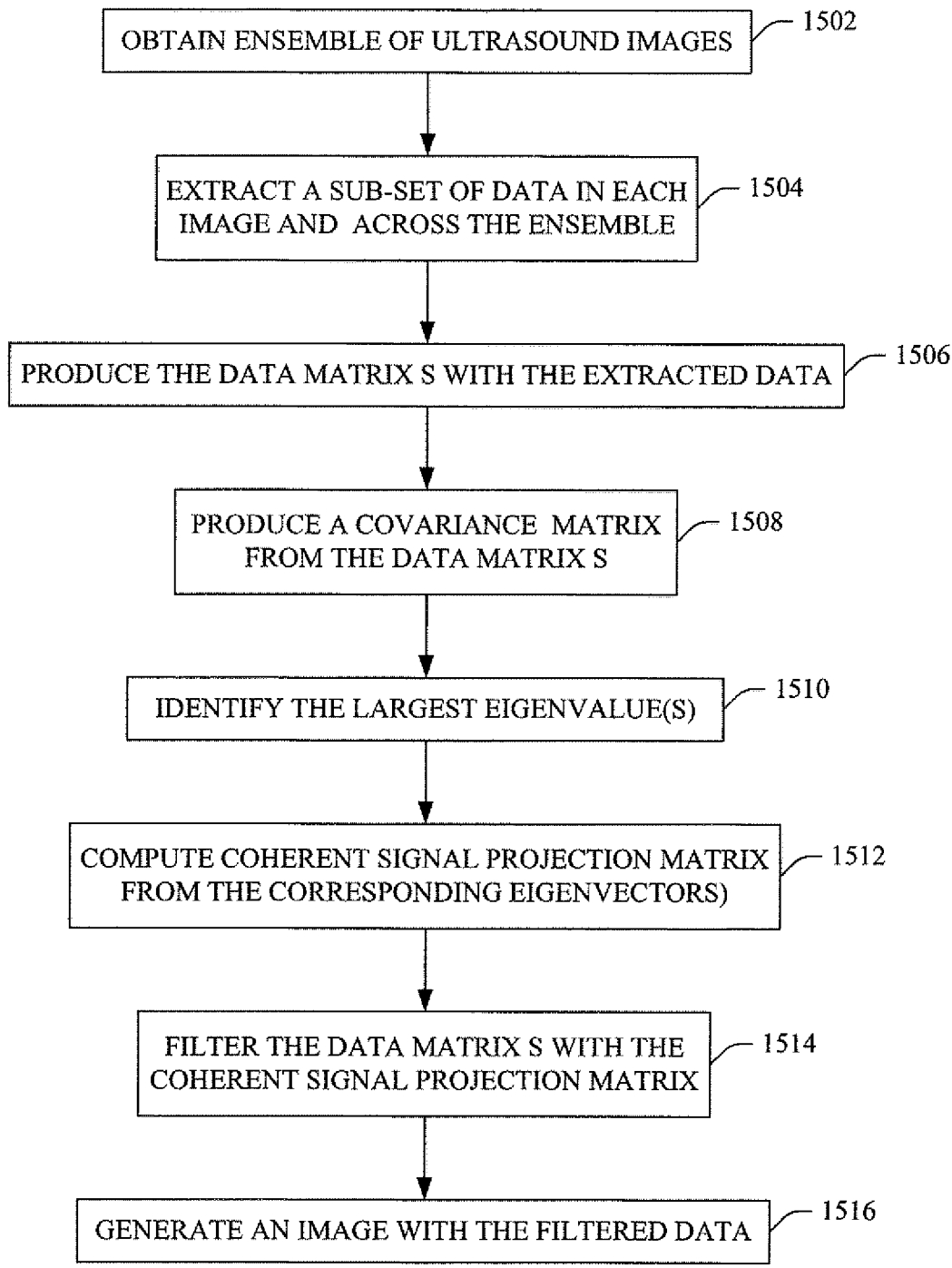
FIG. 15 illustrates an example method in accordance with an embodiment described herein.

FIG. 15 illustrates an example method in accordance with the disclosure herein.

It is to be understood that the following acts are provided for explanatory purposes and are not limiting. As such, one or more of the acts may be omitted, one or more acts may be added, one or more acts may occur in a different order (including simultaneously with another act), etc.

At 1502, an ensemble of ultrasound images is obtained as described herein. The ensemble can be obtained from a signal processor (e.g., the signal processor 110) and/or a storage device such as memory.

At 1504, at least a sub-set of data is extracted from each of the images as described herein and/or otherwise. In one instance, the sub-set is less than all of the data in each image.

At 1506, the data matrix S is produced with the extracted data as described herein and/or otherwise.

At 1508, a covariance matrix is computed for the data matrix S as described herein and/or otherwise. This step may reduce the computational burden of the SVDP filter 214. As described herein, in a variation, this act can be omitted.

At 1510, a largest eigenvalue(s) and corresponding eigenvector(s) are identified in the covariance matrix (or data matrix), as described herein and/or otherwise.

At 1512, a coherent signal projection matrix is computed from the eigenvector(s) of the identified eigenvalue(s) as described herein and/or otherwise.

At 1514, the data matrix S is filtered with the SVDP filter 214, producing the filtered data vector Š, as described herein and/or otherwise.

At 1516, an image is generated with the filtered data (or compounded filtered data) as described herein and/or otherwise.

The above may be implemented by way of hardware and/or a computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An apparatus, comprising:
a memory device with computer readable instructions;
a processor configured to execute the computer readable instructions encoded on the memory device, wherein the processor is configured to, in response to executing the computer readable instructions:
obtain an ensemble of ultrasound images with diversity in an ensemble dimension;
extract a sub-set of data from each of the images;
construct a data matrix with the extracted data, wherein the data matrix has a dimension of space versus the ensemble dimension;
identify a largest eigenvalue(s) and a corresponding eigenvector(s) in the data matrix;
compute a coherent signal projection matrix with the identified corresponding eigenvector(s);
filter the data matrix with the coherent signal projection; and
generate an ultrasound image with the filtered data matrix.

2. The apparatus of claim 1, wherein the ensemble of ultrasound images includes a signal of interest that is coherent across the ensemble dimension, and wherein the ensemble of ultrasound images includes clutter, reverberation, and/or electronic noise across which are incoherent across the ensemble dimension.

3. The apparatus of claim 1, wherein the ensemble of ultrasound images includes images generated from data received in response to transmitted plane waves at different tilt angles, and the data matrix has a dimension of space versus the tilt angle.

4. The apparatus of claim 1, wherein the ensemble of ultrasound images includes images generated from synthetic aperture datasets in response to transmissions from different transmit elements, and the data matrix has a dimension of space versus the transmit element.

5. The apparatus of claim 1, wherein the ensemble of ultrasound images includes images generated with different apodizations, and the data matrix has a dimension of space versus apodization profile.

6. The apparatus of claim 1, wherein the ensemble of ultrasound images includes images generated in response to transmissions from diverging waves, and the data matrix has a dimension of space versus diverging wave, where each diverging wave is defined by its virtual source.

7. The apparatus of claim 1, wherein the ensemble of ultrasound images includes images generated with a fixed transmit focus, and the data matrix has a dimension of space versus transmit event.

8. The apparatus of claim 1, wherein the ensemble of ultrasound images includes images generated from a first stage beamformer, and the data matrix has a dimension of space versus first stage beamformer output.

9. The apparatus of claim 1, wherein the sub-set is less than an entire set of the data from each of the images.

10. The apparatus of claim 1, wherein the sub-set is equal to an entire set of the data from each of the images.

11. The apparatus of claim 1, wherein the ensemble of ultrasound images includes one-dimensional images.

12. The apparatus of claim 1, wherein the ensemble of ultrasound images includes two-dimensional images.

13. The apparatus of claim 1, wherein the ensemble of ultrasound images includes three-dimensional images.

14. The apparatus of claim 1, further comprising:
a transducer array configured to transmit ultrasound signals.

15. The apparatus of claim 14, further comprising:

a signal processor configured to produce the ensemble from echo signals generated in response to the transmitted ultrasound signals and received by the transducer array.

16. A method, comprising:

extracting a sub-set of data from each image of an ensemble of ultrasound images having diversity in an ensemble dimension;

constructing a data matrix with the extracted data, wherein the data matrix has a dimension of space versus the ensemble dimension;

identifying largest eigenvalue(s) in the data matrix;

computing a coherent signal projection matrix with eigenvector(s) of the identified eigenvalue(s);

filtering the data matrix with the coherent signal projection; and generating a decluttered ultrasound image with the filtered data.

17. The method of claim 16, wherein the ensemble of ultrasound images includes a signal of interest that is coherent across the ensemble dimension, and wherein the ensemble of ultrasound images includes clutter, reverberation, and/or electronic noise across which are incoherent across the ensemble dimension.

18. The method of claim 17, further comprising:

computing a covariance matrix with the data matrix, wherein the largest eigenvalue(s) and the corresponding eigenvector(s) are identified from the covariance matrix.

19. The method of claim 17, further comprising:

compounding the filtered data across the ensemble dimension, wherein the decluttered ultrasound image is generated with the compounded filtered data.

20. A non-transitory computer readable medium encoded with computer executable instructions which when executed by a processor causes the processor to:

extract a sub-set of data from each image of an ensemble of ultrasound images having diversity in an ensemble dimension;

construct a data matrix with the extracted data, wherein the data matrix has a dimension of space versus the ensemble dimension;

compute a covariance matrix with the data matrix;

identify largest eigenvalue(s) and a corresponding eigenvector(s) in the covariance matrix;

compute a coherent signal projection matrix with the eigenvector(s) of the identified eigenvalue(s);

filter the data matrix with the coherent signal projection;

compound the filtered data across the ensemble dimension; and generate a decluttered ultrasound image with the compounded filtered data.

* * * * *